(12) United States Patent
Hennessy

(10) Patent No.: US 8,758,326 B2
(45) Date of Patent: Jun. 24, 2014

(54) EMBEDDED WIRE EXTRUSION WITH CONTINUOUS LOOP TIP

(75) Inventor: Eric Richard Hennessy, Lewisville, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 195 days.

(21) Appl. No.: 13/153,043

(22) Filed: Jun. 3, 2011

(65) Prior Publication Data

US 2012/0310214 A1 Dec. 6, 2012

(51) Int. Cl.
*A61M 25/00* (2006.01)

(52) U.S. Cl.
USPC .......................................... 604/527; 600/585

(58) Field of Classification Search
USPC ..................... 604/524–527; 600/585; 606/200
See application file for complete search history.

(56) References Cited

U.S. PATENT DOCUMENTS

| | | |
|---|---|---|
| 5,098,440 A | 3/1992 | Hillstead |
| 5,522,819 A | 6/1996 | Graves et al. |
| 5,769,821 A | 6/1998 | Abrahamson et al. |
| 5,836,947 A * | 11/1998 | Fleischman et al. ............ 606/47 |
| 6,824,553 B1 | 11/2004 | Samson et al. |
| 7,758,592 B2 | 7/2010 | Ayala et al. |
| 2002/0082585 A1 | 6/2002 | Carroll et al. |
| 2005/0192560 A1 | 9/2005 | Walls et al. |
| 2006/0122707 A1 | 6/2006 | McWeeney et al. |
| 2006/0129166 A1 | 6/2006 | Lavelle |
| 2006/0259063 A1 | 11/2006 | Bates et al. |
| 2007/0219466 A1 | 9/2007 | Tremulis et al. |

FOREIGN PATENT DOCUMENTS

| | | |
|---|---|---|
| EP | 0 546 646 A1 | 6/1993 |
| WO | WO 2004/050161 A1 | 6/2004 |
| WO | WO 2008/060529 A2 | 5/2008 |

OTHER PUBLICATIONS

International Search Report and Written Opinion for PCT Application No. PCT/US2012/040419 dated Jul. 13, 2012.

* cited by examiner

*Primary Examiner* — Emily Schmidt
(74) *Attorney, Agent, or Firm* — Brinks Gilson & Lione

(57) ABSTRACT

An elongate medical device includes a tubular member extending between a proximal end and a distal end that has a wall defining a lumen extending therethrough. The elongate medical device also includes a loop portion comprising a plurality of wires having proximal portions embedded into the wall and distal portions which are connected together to form a loop that is distal the distal end of the tubular member.

15 Claims, 6 Drawing Sheets

EMBEDDED WIRE EXTRUSION WITH CONTINUOUS LOOP TIP

TECHNICAL FIELD

The present disclosure generally relates to medical devices, and more particularly to catheters and wire guides having a loop tip.

BACKGROUND

Elongate medical devices used in interventional procedures, such as catheters and wire guides, navigate through a path inside a body cavity, duct, or vessel of a patient toward a point of treatment. A wire guide may be inserted into the patient and define the path. After the wire guide is positioned within the patient, another medical device, such as a catheter, is placed over the wire guide and moved along the length of the wire guide toward the point of treatment. The paths are often long and tortuous due to the presence of natural bends and/or curves, or unnatural impediments, such as tumors, build-ups, and/or strictures. The presence of a tortuous path may make navigation of the elongate medical device difficult. Additionally, a tortuous path may increase the likelihood that the elongate medical device traumatizes an inner wall of the body cavity, duct, or vessel as the device navigates through the path.

Elongate medical devices have a degree of flexibility in order to navigate through the a tortuous path. However, if the medical devices are too flexible, they are prone to kinking, which hinders the device's ability to navigate through the paths. In addition, the more flexibility the medical device has, the less torqueability the device has, which makes curving or turning the device through the bends or around the impediments in the path more difficult.

BRIEF SUMMARY

The present disclosure describes an elongate medical device such as a catheter that includes a tubular member extending between a proximal end and a distal end, and that has a wall that defines a lumen extending therethrough. The medical device also includes a loop portion that comprising a plurality of wires having proximal portions embedded into the wall, and distal portions which are connected together to form a loop. The loop is disposed distal the distal end of the tubular member. In one example, the proximal portions of the plurality of wires may comprise a stiffening portion of the tubular member that reduces the flexibility of the medical device. The stiffening portion may comprise a coil that is helically disposed about the lumen. Alternatively, the stiffening portion may comprise a tubular braid circumferentially disposed about the lumen. In another example, the proximal portions of the plurality of wires are embedded only a distal end of the wall. In one example, the plurality of wires proximally extends about one centimeter from the distal end of the wall.

The plurality of wires may comprise a first set of wires distally extending from the distal end of a first side of the tubular member, and a second set of wires distally extending from the distal end of a second side of the elongate outer portion. A distal end of the first set of wires may be connected to a distal end of the second set of wires to form the loop. The proximal portions of the plurality of wires may also include a transition portion that distally extends from the stiffening portion to the distal end of the tubular member. The transition portion may be longitudinally disposed in the wall. A distal end of the transition portion may be connected to a proximal end of the distal portions of the plurality of wires at the distal end of the tubular member.

A proximal end of the first set of wires and a proximal end of the second set of wires may be disposed about the lumen at the distal end of the tubular member. The first set of wires may be disposed opposite the second set of wires about the lumen, and/or may be disposed entirely around the lumen. Distal portions of the first and second sets of wires may be twined. In addition or alternatively, the distal portions of the first and second sets of wires may be covered with a sheath.

In one example, the lumen may comprise a central hollow lumen extending through the tubular member. In another example, a core wire may be disposed in the lumen, where a cross section of the tubular member comprises a solid cross section. A distal portion of the wall may comprise a tapered portion, and the transition portion of the plurality of wires proximally extends to a proximal end of the tapered portion.

DETAILED DESCRIPTION

Figure 1:
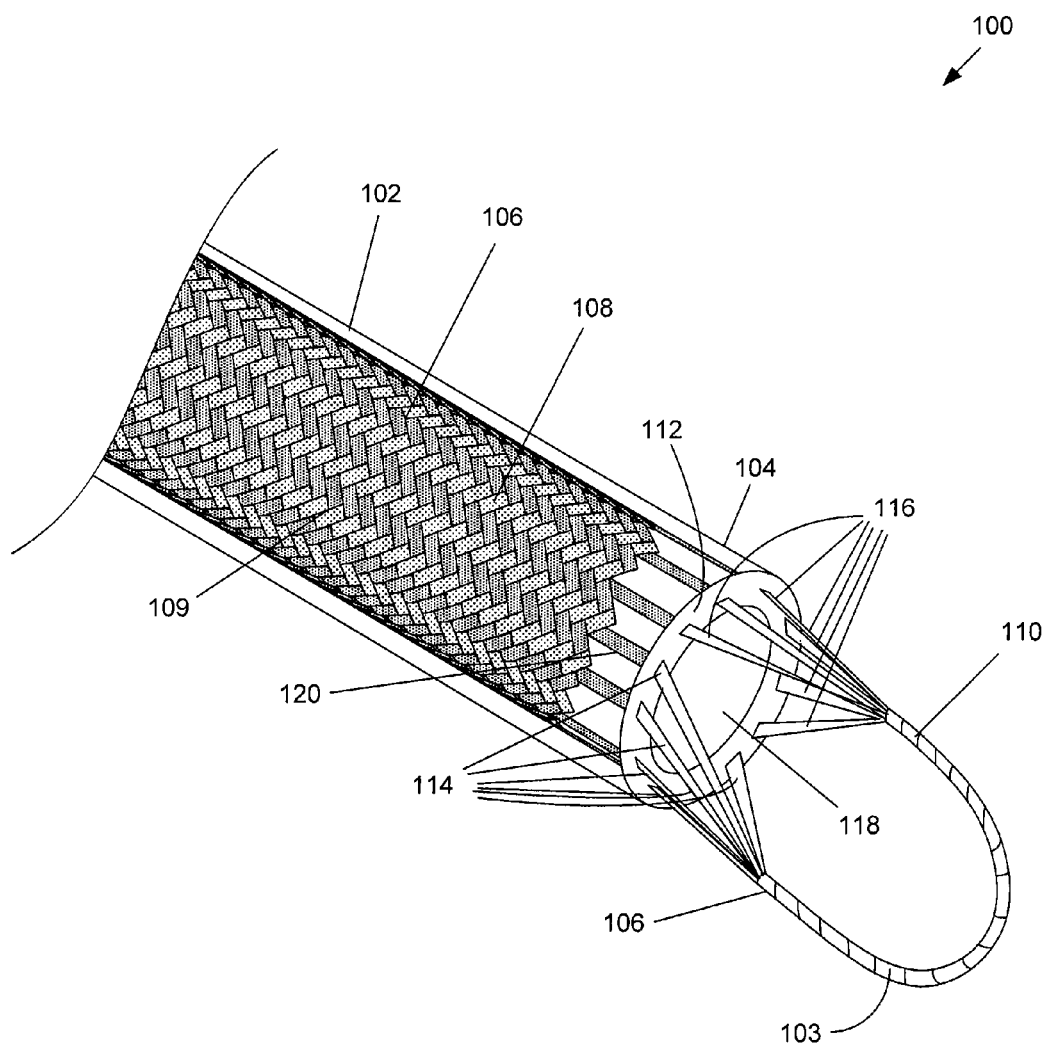
FIG. 1 shows a perspective view of a distal portion of a catheter 100 having a plurality of wires, where a proximal portion of the plurality of wires is embedded in the catheter and a distal portion forms a loop tip past a distal end of the catheter, and where the proximal portion of the wires comprises a tubular braided configuration.

The present disclosure describes an elongate medical device used in interventional procedures that has a plurality of wires comprising a proximal portion that is embedded in the elongate medical device and a distal portion that is configured as a loop tip extending from a distal end of the elongate medical device. The embedded proximal portion may function as a stiffening portion. By embedding the plurality of wires in the elongate medical device, the stiffness of the medical device may be increased, which increases the medical device's resistance to kinking and also improves the medical device's torqueability as the medical device is maneuvered through the paths of bodily vessels within a patient.

Additionally, the loop distally extending from the distal end of the medical device provides a looped tip for the medical device. The looped tip may reduce the medical device's ability to traumatize the inner walls of the bodily vessels as the medical device is navigated through the paths of the bodily vessels. Alternatively or in addition, the looped tip may provide a mechanism that facilitates navigation through the bodily vessels. For example the medical device may comprise a catheter having a hollow central lumen, and the looped tip may facilitate navigation of the catheter through the bodily vessels without the catheter being guided over a wire guide. Alternatively or in addition, the wire guide may couple to the looped tip for navigation of the wire guide and the catheter through the bodily vessels. Alternatively or in addition, the looped tip may function as a grasping tip that may be grasped by another medical device. For example, the medical device may comprise a catheter or a feeding tube that is inserted during a percutaneous endoscopic gastrostomy. Another medical device, such as a pair of forceps, may grasp the grasping tip and pull the catheter or feeding tube to a desired position within the patient.

A plurality of wires having a proximal portion that is embedded in the medical device and a distal portion that forms a loop extending from the distal end of the medical device provides a single set of wires that enhances the medical device's resistance to kinking and torqueability, while also reducing the medical device's ability to traumatize the inner walls of bodily vessels. Using a single set of wires may reduce manufacturing time and/or costs. In addition, forming a loop tip at the distal end of the medical device from wires embedded in the medical device may provide a loop tip with a more secure connection to the medical device than a loop tip that is attached to the medical device using known techniques, such as bonding, applying adhesives, or using movable and/or removable members. Alternatively or in addition, the embedded wires may be evenly distributed in the medical device. The even distribution may provide an evenly distributed load on the medical device where the looped tip is pulled.

The elongate medical device may comprise a tubular outer portion and a central lumen longitudinally extending through the outer portion. In one example, the central lumen may be hollow. In an alternative example, a core wire may disposed in the central lumen and the medical device comprises a solid cross section.

The following description refers to the elongate medical device as a catheter having a tubular member and a central lumen longitudinally extending through the tubular member. However, the following description is not limited to catheters and is equally applicable to elongate medical devices such as wire guides in which the central lumen is replaced with a solid material, such as nitinol.

FIG. 1 shows a perspective view of a distal portion 102 of a catheter 100 having a loop tip 103. The catheter 100 includes an elongate tubular member 104 and a plurality of wires 106. The plurality of wires 106 includes a proximal portion 108 and a distal portion 110. The proximal portion 108 is embedded in the tubular member 104. The distal portion 110 comprises a loop distally extending from a distal end 112 of the tubular member 104. The distal portion 110 of the plurality of wires 106 includes a first set of wires 114 and a second set of wires 116. The first set of wires 114 extends from the distal end 112 on one side of the tubular member 104. Similarly, the second set of wires 116 extends from the distal end 112 on another side of the tubular member 104.

From an alternative perspective, the plurality of wires 106 may be considered a single set of wires that comprises a first subset of wires 114 and a second subset of wires 116. In one example, the first set of wires 114 extends from the distal end 112 on one side of the tubular member 104, and the second set of wires 116 extends from the distal end 112 on another side of the tubular member 104. The first subset of wires 114 and the second subset of wires 116 may be bound together when embedded in the tubular portion.

The wires in the first set of wires 114 may be stranded together for at least a distal portion of the first set of wires 114. Similarly, the wires in the second set of wires 116 may be stranded together for at least a distal portion of the second set of wires 116. In one example embodiment, the stranded portions are twined or twisted together. In another example embodiment, the stranded portions are covered with a sheath. The sheath may be made of a polymer such as plastic, elastomer, or silicone. Other polymers or other non-polymer materials that keep the wires stranded together may be used. In another example embodiment, the stranded portions of the wires 106 are both stranded together and covered with a sheath. A distal end of the first set of wires 114 is in connection with a distal end of the second set of wires 116 to form the loop top 103. The distal ends of the first and second sets of wires 114, 116 may be connected using any suitable technique, such as by twisting them together, soldering them together, or using any known adhesive or bonding material.

As shown in FIG. 1, the distal portion 110 of the plurality of wires 106 distally extends from the proximal portion 108, which is embedded in the elongate tubular member 104. The proximal portion 108 may include a stiffening portion 109 that decreases the flexibility of the catheter 100. The length of the stiffening portion 109 may vary and may depend on the desired flexibility of the catheter 100. The stiffening portion 109 may proximally extend from a position in the distal portion 102 to any portion within the catheter 100. FIG. 1 shows an example configuration of the proximal portion 108 having a tubular braided configuration. The plurality of wires 106 are woven together to form the tubular braid. The tubular braid is disposed in the tubular member 104 around a central lumen 118 of the catheter 100. As shown in FIG. 1, at the distal end 112 of the tubular member 104, the plurality of wires 106 includes a middle transition portion 120 disposed in between the proximal portion 108 and the distal portion 110, in which the plurality of wires 106 transitions from the proximal tubular braid to the distal loop outside of the tubular member 104. The wires in the middle portion 120 are longitudinally disposed in the tubular member 104. The distal portion 110 extends from the middle portion 120 and distally beyond the distal end 112 to form the loop tip 103. As shown in FIG. 1, all of the wires making up the tubular braid are longitudinally disposed at the distal end 112 of the catheter 100 and distally extend past the distal end 112 to form the loop. Alternatively, less than all of the wires making up the tubular braid distally are longitudinally disposed at the distal end 112 of the catheter 100 and extend past the distal end 112 to form the loop.

FIG. 1 shows the plurality of wires 106 comprising twelve wires, with the first set of wires 114 and the second set of wires 116 each comprising six wires. However, twelve wires is an exemplary number of wires and other amounts of wires may be used. The number of wires may depend on the size of the wires, the material of the wires, and/or the size of the catheter 100. Alternatively or in addition, the number of wires may depend on the desired stiffness of the catheter. The stiffness of the catheter 100 increases with the more wires that are used. During extrusion of the catheter 100, the portions of the wires 106 that are disposed within the tubular member 104, including the proximal tubular braid 108 and the middle portion 120, are placed over a mandrel or pin and the molten polymer making up the tubular member 104 is applied around the tubular braid 108 and the longitudinally extending wires 120. In an embodiment where the central lumen 118 is replaced with a core made of a solid material such as nitinol, the core is manufactured first. Subsequently, the portions of the wires 106 that are to be disposed in the outer member are placed over the solid core, and the molten polymer making up the outer member is applied over the solid core and the portion of the wires.

Figure 2A:
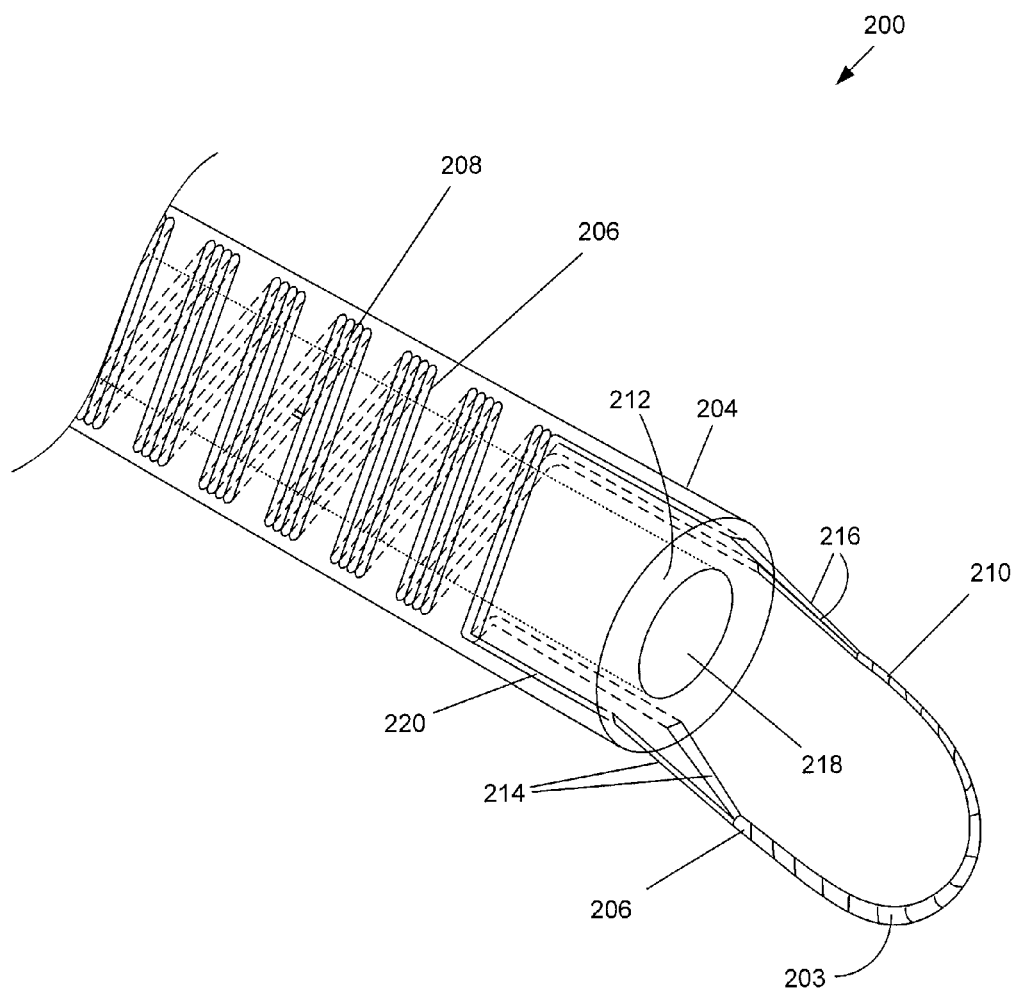
FIG. 2A shows a perspective view of an alternative catheter, where the proximal portion of the wires comprises a coil portion that is helically disposed about a central lumen of the catheter, and where the coils of the coil portion are spaced apart.
Figure 2B:
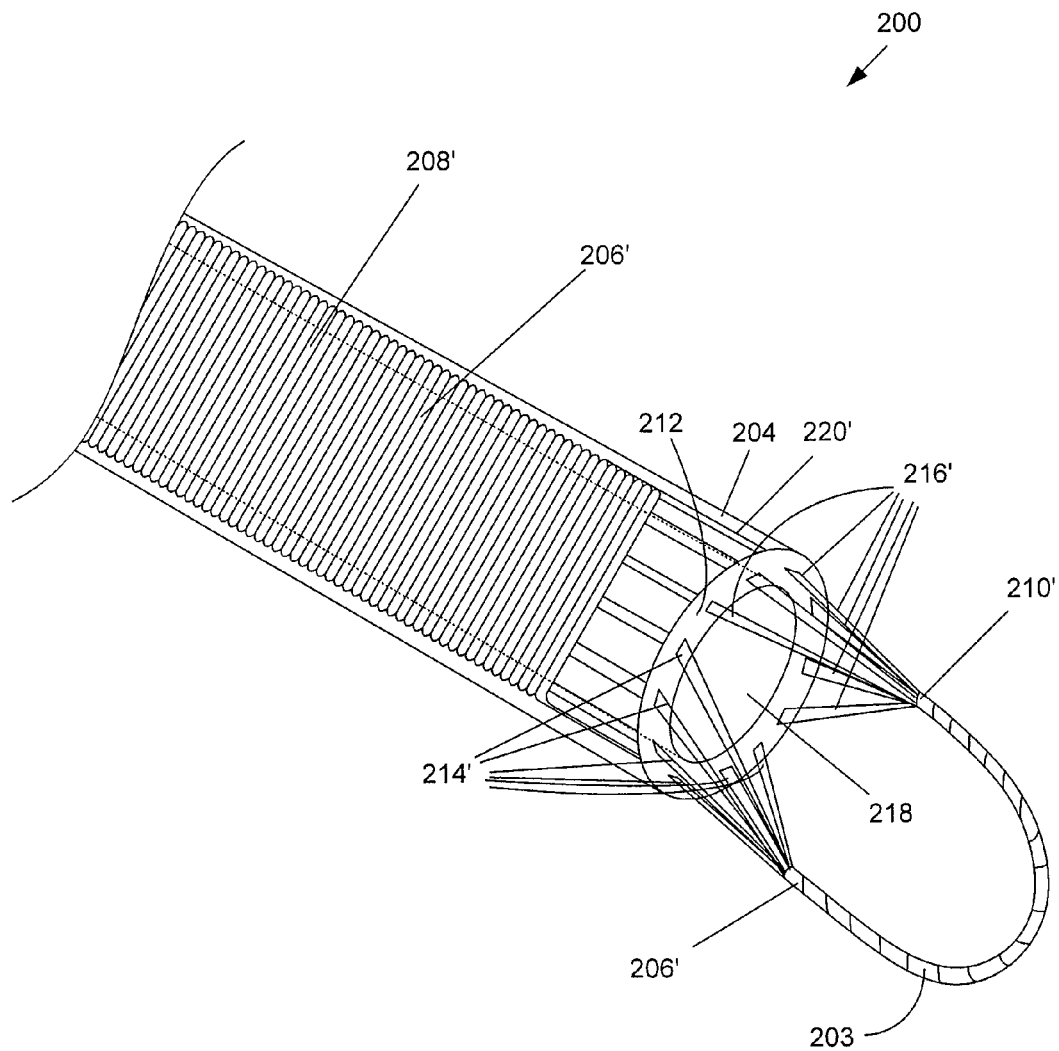
FIG. 2B shows a perspective view of an alternative catheter, where the proximal portion of the wires comprises a coil portion that is helically disposed about a central lumen of the catheter, and where the coils of the coil portion are in contact with each other.

FIGS. 2A-2B show an alternative configuration of the proximal portion 108 of the plurality of wires 106 shown in FIG. 1. FIGS. 2A-2B show a proximal portion 208 of a plurality of wires 206, 206' embedded in a tubular member 204 of a catheter 200 as a coil. As shown in FIGS. 2A-2B, the wires 206, 206' are helically disposed about a central lumen 218 of the catheter 200. At a distal end 212 of the catheter 200, the plurality of wires 206, 206' includes a middle portion 220, 220' in which the plurality of wires 206, 206' are longitudinally disposed about the central lumen 218. At the middle portion 220, 220', the plurality of wires 206, 206' transitions from the proximal coil 208, 208' to the distal loop 210, 210' outside of the tubular member 204. All or at least some of the wires 206, 206' included in the proximal coil are included as part of the middle portion 220, 220' and/or as part of the distal portion 210, 210' that extends past the distal end 212 of the catheter 200 and forms the loop.

The distal portion 210, 210' of the plurality of wires 206, 206' includes a first set of wires 214, 214' and a second set of wires 216, 216'. In FIG. 2A, two of the four wires comprise the first set of wires 214, and the other two of the four wires comprise the second set of wires 216. In FIG. 2B, six of the twelve wires comprise the first set of wires 214', and the other six of the twelve wires comprise the second set of wires 216'. Similar to the first and second sets of wires 114, 116 as shown in FIG. 1, a distal end of the first set of wires 214, 214' is in connection with a distal end of the second set of wires 216, 216' to form the loop 203. The amount of wires included in the coil configuration may vary. Although four wires and twelve wires are shown in FIGS. 2A and 2B respectfully, four wires and twelve wires are exemplary amounts and other amounts of wires may be used. The amount of wires may depend on a desired stiffness of the catheter 200. The more wires that are disposed in the tubular member 204, the greater the stiffness of the catheter 200.

In addition, the tightness of the coil configuration may vary depending on the spacing between the coils. In general, the closer to each other that the coils are disposed, the tighter the coil. FIG. 2A shows the coils spaced apart from each other. In FIG. 2B, there is no spacing in between the coils. The coil configuration of the wires 206' provides the catheter 200 with relatively more stiffness than the coil configuration of the wires 206 shown in FIG. 2A.

During extrusion of the catheter 200, the portions of the wires 206, 206' that are disposed within the tubular member 204, including the proximal coiled portion 208 and the middle portion 220, 220', are placed over a mandrel or pin and the molten polymer making up the tubular member 204 is applied around the coiled portion of the wires 206, 206' and the middle portion 220, 220'. In an embodiment where the central lumen 218 is replaced with a core made of a solid material such as nitinol, the core is manufactured first. Subsequently, the portions of the wires 206, 206' that are to be disposed in the outer member are placed over the solid core, and the molten polymer making up the outer member is applied over the solid core and the portion of the wires.

Figure 3:
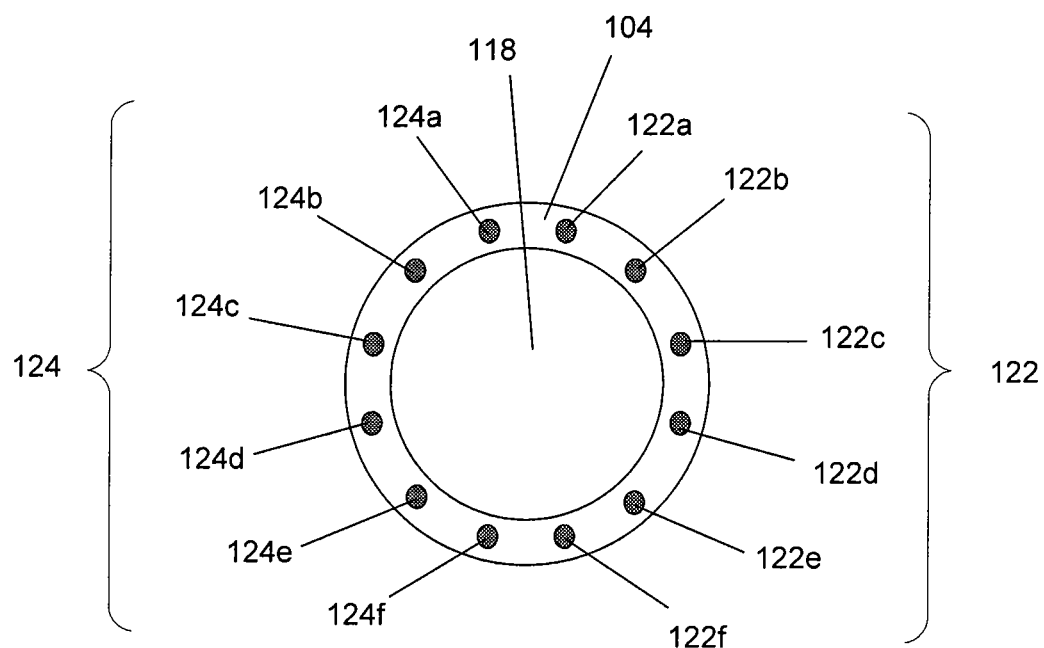
FIG. 3 shows a cross-sectional axial view of the catheter at the distal end of the catheter, shown proximally extending from the distal end, and illustrating two sets of wires disposed opposite each other in the outer member of the catheter.

FIG. 3 shows a cross-sectional axial view of the catheters 100, 200 at the distal ends 112, 212, illustrating the middle transition portions 120, 220, 220' of the wires 106, 206, 206' in FIGS. 1, 2A, and 2B longitudinally disposed at the respective distal ends 112, 212. For simplicity purposes, the following description with reference to FIG. 3 refers to the catheter 100 shown in FIG. 1. Nonetheless, the following description and the cross-sectional view of FIG. 3 are equally applicable to the catheter 200 shown in FIGS. 2A, 2B. As shown in FIG. 3, the middle transition portion 120 of the wires 106 includes a first set 122, including wires 122a, 122b, 122c, 122d, 122e, 122f, and a second set 124, including wires 124a, 124b, 124c, 124d, 124e, 124f. The first set of wires 122 is connected to the first set of wires 114 of the distal portion 110 (shown in FIG. 1), and the second set of wires 124 of the middle portion 120 is connected to the second set of wires 116 of the distal portion 110 (shown in FIG. 1). The first set of wires 122 and the second set of wires 124 are longitudinally disposed opposite each other about the central lumen 118 in the tubular member 104 of the catheter 100. In addition, the two sets of wires 122, 124 are circumferentially disposed about the entire circumference of the central lumen 118. Also, as shown in FIG. 3, the distance between two adjoining wires is the same for all of the wires in the first set of wires 122 and the second set of wires 124. For example, the distance between wire 122a and wire 122b is the same as the distance between wires 122b and 122c, and between wires 122a and 124a.

Figure 4:
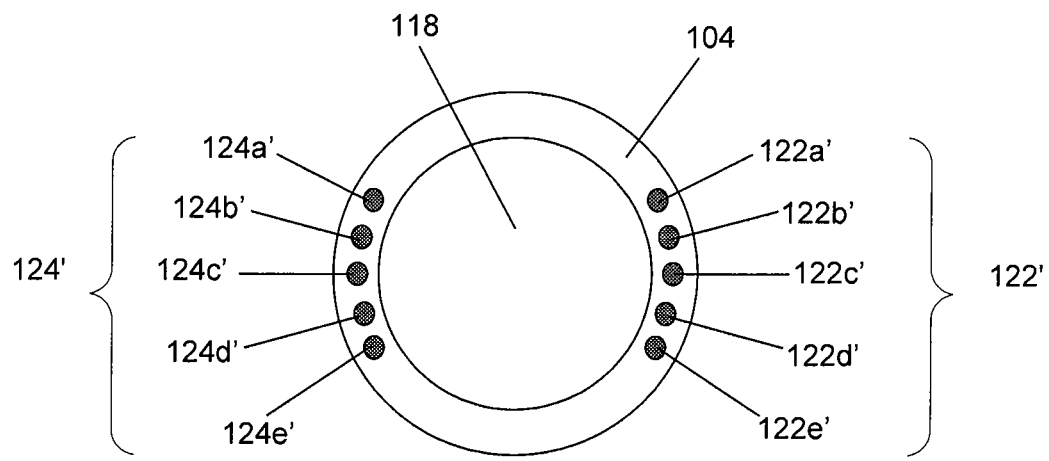
FIG. 4 shows a cross-sectional axial view of the catheter at the distal end of the catheter, shown proximally extending from the distal end, and illustrating two sets of wires disposed entirely around the central lumen.

FIG. 4 shows a cross-sectional axial view of an alternative configuration of the middle transition portions 120, 220, 220' shown in FIGS. 1, 2A, and 2B. As with FIG. 3, for simplicity purposes, the following description with reference to FIG. 4 refers to the catheter 100 shown in FIG. 1. Nonetheless, the following description and the cross-sectional view of FIG. 4 are equally applicable to the catheter 200 shown in FIGS. 2A-2B. The first set of wires 122' of the middle transition portion 120 and the second set of wires 124' of the middle transition portion 120 are longitudinally disposed opposite each other in the tubular member 104 of the catheter 100. Additionally, as shown in FIG. 4, the first set of wires 122' are disposed equidistant from the second set of wires 124' about the central lumen 118. For example, the circumferential distance about the central lumen 118 measured in a clockwise direction from wire 124c' to 122c' is equal to the circumferential distance about the central lumen 118 measured in the clockwise direction from wire 122c' to 124c'. However, unlike the configuration of the middle section 120 as shown in FIG. 3, the configuration of the first set of wires 122' and the second set of wires 124' of the alternate configuration as shown in FIG. 4 are not disposed about the entire circumference of the central lumen 118. In addition, the distances between adjoining wires in the alternate configuration of the middle portion 120 as shown in FIG. 4 are not all the same. For example, the circumferential distance between wires 122a' and 122b' is not the same as the circumferential distance between wires 122a' and 124a'.

FIGS. 3 and 4 show configurations of the middle portion 120 in which the first set of wires 122, 122' of the middle portion 120 and the second set of wires 124, 124' of the middle portion 120 are longitudinally disposed opposite each other in the tubular member 104 of the catheter 100. A distance from a middle position of the first set of wires 122, 122' (e.g., wire 122c, 122c') to a middle position of the second set of wires 124, 124' (e.g., wire 124c, 124c') determined in a clockwise direction is the same as the distance from the middle position of the first set of wires 122, 122' (e.g., wire 122c, wire 122c') to a middle position of the second set of wires 124, 124' (e.g., wire 124c, 124c') determined in a counter-clockwise direction. However, in another configuration, the wires 122, 122' and 124, 124' may be longitudinally disposed about the central lumen such that the distance from wire 122c, 122c' to wire 124c, 124c' measured in a clockwise direction is not the same as the distance from wire 122c, 122c' to wire 124c, 124c' measured in a counter-clockwise direction. Additionally, FIGS. 3 and 4 show configurations of the middle portion 120 in which the number of wires comprising the first set 122, 122' is the same as the number of wires comprising the second set 124, 124'. However, in another configuration, the number of wires comprising the first set 122, 122' is different than the number of wires comprising the second set 124, 124'.

Figure 5:
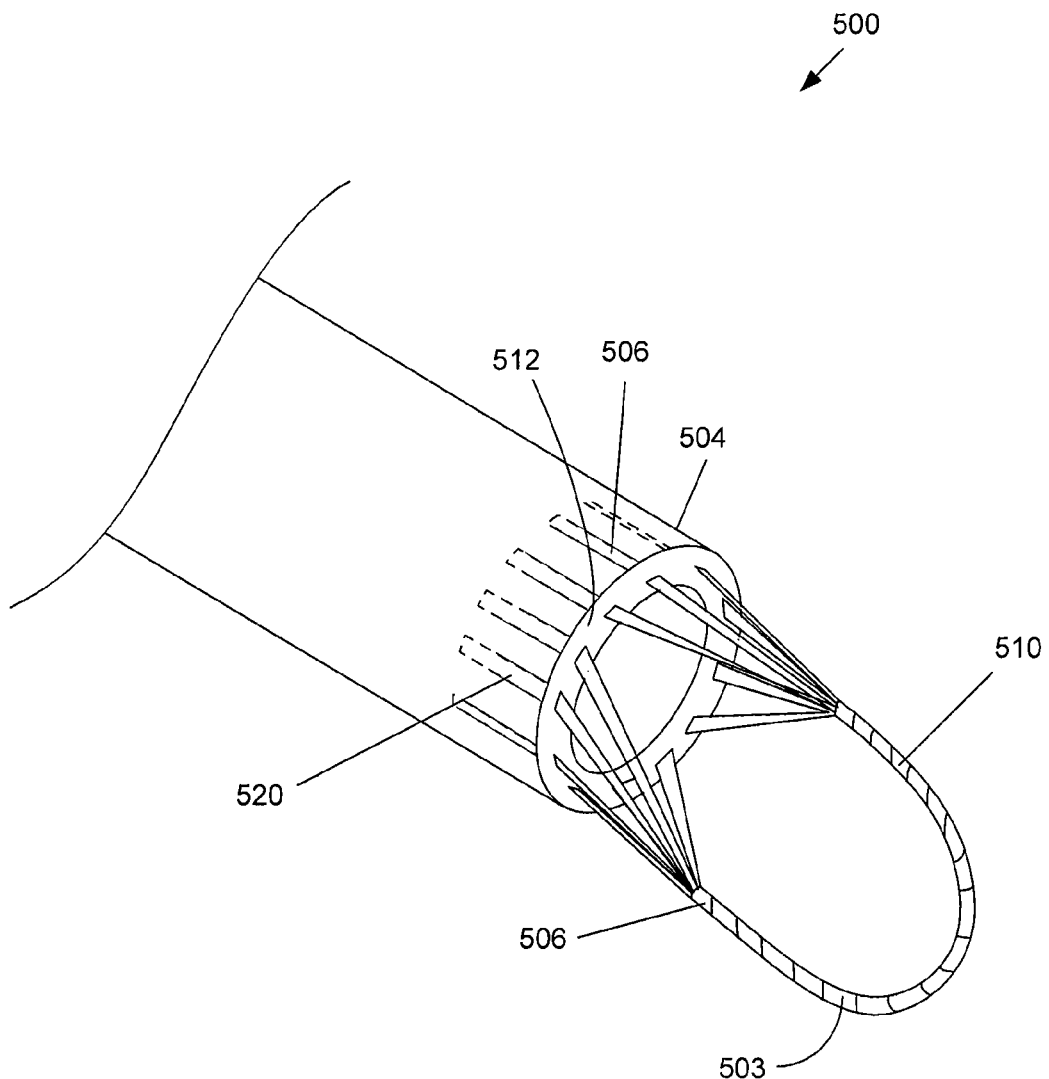
FIG. 5 shows a perspective view of an alternative catheter having a loop tip, where the proximal portion of the wires are longitudinally embedded in the tubular member and terminal at a position proximal the distal end of the catheter.

FIG. 5 shows a perspective view of an alternative embodiment of a catheter 500 having a loop tip 503. The catheter 500 includes an elongate tubular member 504 and a plurality of wires 506. In comparison with the plurality of wires 106, 206, 206' for the catheters 100 and 200 shown in FIGS. 1, 2A, and 2B, the plurality of wires 506 for the catheter 500 does not include a proximal portion configured as a tubular braid or a coil. As shown in FIG. 5, the plurality of wires 506 includes an embedded portion 520 and a loop portion 510 that distally extends from the embedded portion 520. The embedded portion 520 is longitudinally embedded in the tubular member 504 at the distal end 512 of the catheter 500. The embedded portion 520 proximally at least one centimeter from the distal end 512 of the catheter 500. The loop portion 510 comprises a loop distally extending past a distal end 512 of the tubular member 504 and forming a loop tip 503.

Figure 6:
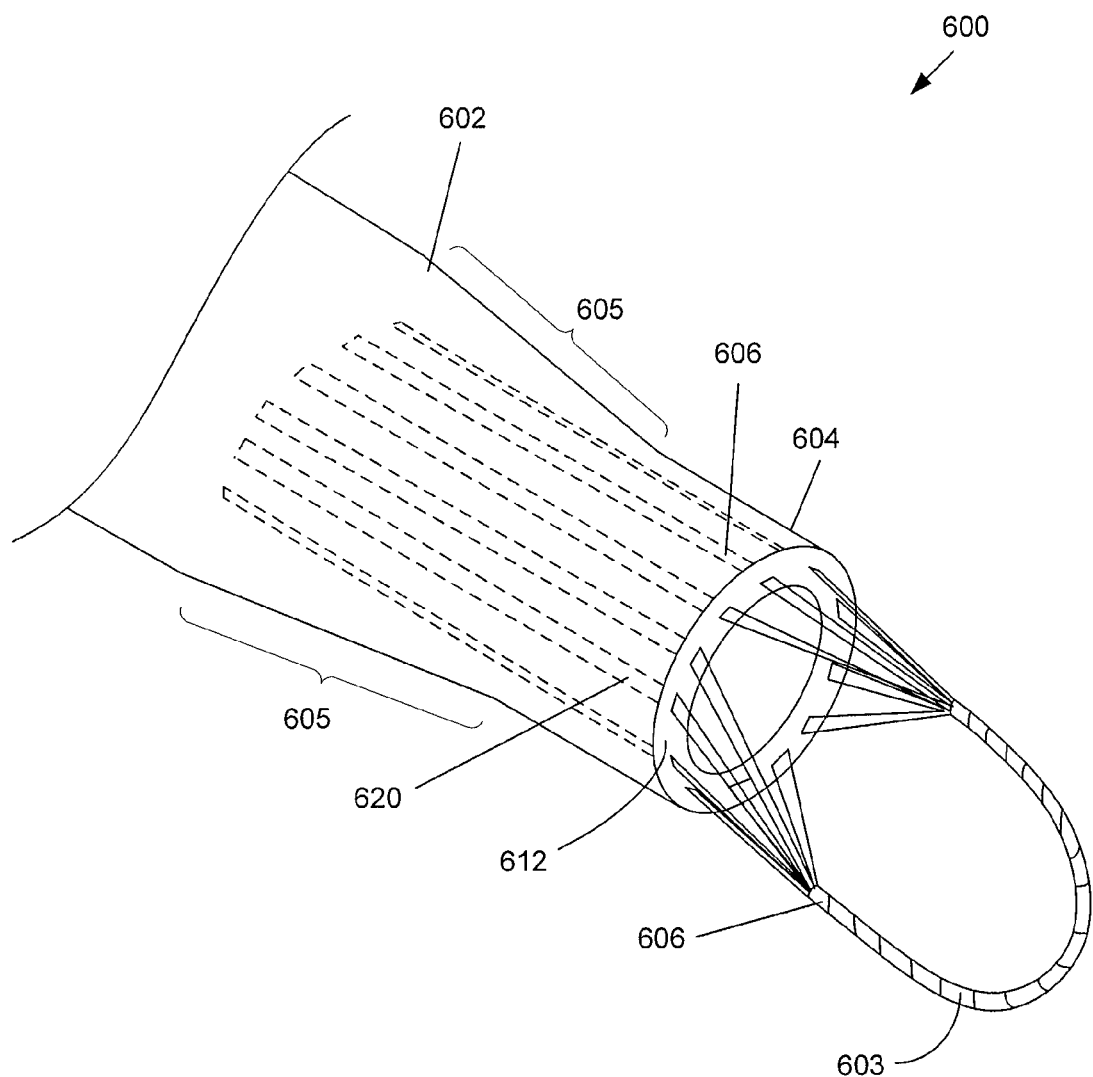
FIG. 6 shows a perspective view of an alternative catheter having a loop tip, where the distal portion of the catheter comprises a tapered portion.

FIG. 6 shows a perspective view of an alternative catheter 600 having a loop tip 603, where a distal portion 602 of the catheter 600 includes a tapered portion 605. In general, it may be desirable for a catheter to have a certain degree of stiffness over the middle and/or proximal portions of the catheter in order for the catheter to have optimal maneuverability through the paths of the bodily vessels. However, it may not be desirable for the catheter to have that same degree of stiffness at the distal portion 602. FIG. 6 illustrates a catheter 600 in which the distal portion 602 includes a tapered portion 605 so that the distal portion 602 has a smaller diameter and is more flexible than the middle and/or proximal portions of the catheter. As shown in FIG. 6, the diameter of the catheter 600 at a proximal end of the tapered portion 605 is greater than the diameter of the catheter 600 at a distal end of the tapered portion 605. In addition, FIG. 6 shows the distal end of the tapered portion being located proximal the distal end 612 of the tubular member 604. Alternatively, the distal end of the tapered portion 605 may be positioned at the distal end 612 of the tubular member 604. The length of the tapered 605 portion may vary and the length may depend on the length of the catheter 600, the diameter of the catheter, and/or the use or medical procedure for which the catheter 600 is intended. In one example, the tapered portion is fifteen centimeters long.

FIG. 6 shows a proximal portion 620 of a plurality of wires 606 embedded in the tubular member 604. The proximal portion 620 may proximally extend to the proximal end of the tapered portion 605. However, other configurations may be used. For example, the proximal portion 620 may proximally extend proximally past the proximal end of the tapered portion 605, in between the proximal end and the distal end of the tapered portion 605, or distal the distal end of the tapered portion 605. In addition, FIG. 6 shows the plurality of wires 606 to have a configuration similar to the configuration of the plurality of wires 506 shown in FIG. 5, in that the plurality wires 606 does not include a stiffening portion, such as a tubular braid or a coil as shown in FIGS. 1, 2A, and 2B. However, the plurality of wires 606 may be configured to have any configuration in accordance with the embodiments of the catheters 100, 200 as shown in FIGS. 1, 2A, 2B, or 5. As examples, the plurality of wires 606 may include a stiffening portion, such as a tubular braid or a coil shown in FIGS. 1, 2A or 2B that is in connection with a proximal end of the wires 620. The longitudinal placement of the stiffening portion within the tubular member 604 may depend on how far the wires 620 proximally extend from the distal end 612 of the tubular member. Based on how far the wires 620 proximally extend from the distal end 612, a distal end of the stiffening portion may be at, proximal, or distal the proximal end of the tapered portion 605.

Any suitable material can be used for the plurality of wires 106, 206, 206'. The material chosen needs to be biocompatible and able to be formed into the structures described herein. Examples of suitable materials includes nitinol and stainless steel. Also, the cross section of the wires may be round and/or flat.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

I claim:

1. An elongate catheter comprising:
    a tubular member extending between a proximal end and a distal end, the tubular member having a wall that defines a lumen extending therethrough; and
    a loop portion comprising a plurality of wires having proximal portions embedded into the wall, and distal portions which are connected together to form a loop, the loop being distal the distal end of the tubular member,
    wherein the proximal portions of the plurality of wires comprise a stiffening portion of the tubular member that reduces the flexibility of the medical device, and
    wherein the stiffening portion comprises a tubular braid circumferentially disposed about the lumen.

2. The catheter of claim 1, wherein the distal portions of the plurality of wires comprises: a first set of wires distally extending from the distal end of a first side of the tubular; and a second set of wires distally extending from the distal end of a second side of the tubular member, wherein a distal end of the first set of wires is connected to a distal end of the second set of wires to form the loop.

3. The catheter of claim 2, wherein the proximal portions of the plurality of wires further comprise a transition portion that distally extends from the stiffening portion to the distal end of the tubular member, wherein the transition portion is longitudinally disposed in the wall, and wherein a distal end of the transition portion is connected to a proximal end of the distal portions of the plurality of wires at the distal end of the tubular member.

4. The catheter of claim 2, wherein a proximal end of the first set of wires and a proximal end of the second set of wires are disposed about the lumen at the distal end of the tubular member.

5. The catheter of claim 4, wherein the first set of wires is disposed opposite the second set of wires about the lumen.

6. The catheter of claim 4, wherein the first set of wires and the second set of wires are disposed entirely around the lumen.

7. The catheter of claim 2, wherein a distal portion of the first set of wires is twined, and a distal portion of second set of wires is twined.

8. The catheter of claim 2, wherein a distal portion of the first set of wires and a distal portion of the second set of wires are covered with a sheath.

9. The catheter of claim 1, wherein the lumen comprises a hollow central lumen extending through the wall.

10. The catheter of claim 1, wherein a core wire is disposed in the lumen.

11. The catheter of claim 10, wherein a cross section of the tubular member comprises a solid cross section.

12. The catheter of claim 3, wherein a distal portion of the wall comprises a tapered portion, and wherein the transition portion of the proximal portion of the plurality of wires proximally extends to a proximal end of the tapered portion.

13. An elongate medical device comprising:
an elongate tubular member extending from a proximal end to a distal end, the tubular member having a wall that defines a lumen extending therethrough; and
a plurality of wires comprising:
a proximal portion longitudinally disposed in the wall; and
a distal portion comprising a loop that distally extends from the proximal portion past the distal end of the wall,
wherein the proximal portion of the plurality of wires comprises a stiffening portion of the tubular member that reduces the flexibility of the medical device, and
wherein the stiffening portion comprises a tubular braid circumferentially disposed about the lumen.

14. The medical device of claim 13, wherein the lumen comprises a hollow central lumen.

15. The medical device of claim 13, wherein a core wire is disposed in the lumen.

* * * * *